US012114860B2

United States Patent
Pic et al.

(10) Patent No.: US 12,114,860 B2
(45) Date of Patent: Oct. 15, 2024

(54) DEVICES, SYSTEMS, AND METHODS FOR SECURING TISSUE

(71) Applicant: Boston Scientific Scimed, Inc., Maple Grove, MN (US)

(72) Inventors: Andrew Pic, Northboro, MA (US); John T. Favreau, Spencer, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 16/953,625

(22) Filed: Nov. 20, 2020

(65) Prior Publication Data
US 2021/0153869 A1    May 27, 2021

Related U.S. Application Data (60) Provisional application No. 62/941,003, filed on Nov. 27, 2019.

(51) Int. Cl.
*A61B 17/12* (2006.01)
(52) U.S. Cl.
CPC .............................. *A61B 17/12013* (2013.01)
(58) Field of Classification Search
CPC ...... A61B 17/0467; A61B 2017/00296; A61B 2017/0488; A61B 2017/306; A61B 17/0487; A61B 2017/06176; A61B 17/12013; A61B 17/32056; A61B 2017/00269; A61B 2017/0464; A61B 2017/0496; A61B 2017/12018;
(Continued)

(56) References Cited

U.S. PATENT DOCUMENTS

| 4,592,355 A | 6/1986 | Antebi |
| 4,955,913 A | 9/1990 | Robinson |
| 5,520,691 A | 5/1996 | Branch |

(Continued)

FOREIGN PATENT DOCUMENTS

| EP | 0701797 A2 | 3/1996 |
| WO | 2018132801 A1 | 7/2018 |

OTHER PUBLICATIONS

"About." Merriam-Webster.com Dictionary, Merriam-Webster, https://www.merriam-webster.com/dictionary/about. Accessed Oct. 5, 2022.*

(Continued)

*Primary Examiner* — Katherine H Schwiker
*Assistant Examiner* — Lauren Dubose
(74) *Attorney, Agent, or Firm* — Seager, Tufte & Wickhem, LLP (57) ABSTRACT

The present disclosure pertains to medical devices. More particularly, the present disclosure pertains to devices, systems, and methods for securing tissue, such as a tissue defect or wound resulting from an endoscopic procedure, e.g., an endoscopic mucosal resection or submucosal dissection procedure. In one example, a device for securing tissue may include a loop portion configured to be disposed about a distal end of a delivery device in a delivery configuration and configured to be secured about the tissue in a deployed configuration. A locking member may be disposed on the loop portion. A tether portion having a proximal end extendable proximally within the delivery device and a distal portion extending from the loop portion slidably through the locking member.

20 Claims, 6 Drawing Sheets

(58) Field of Classification Search
CPC .. A61B 2017/12004; A61B 2018/1407; A61B 2017/0475; A61B 1/00089
USPC ........................................................ 606/228
See application file for complete search history.

(56) References Cited

U.S. PATENT DOCUMENTS

| | | | |
|---|---|---|---|
| 6,136,009 | A | 10/2000 | Mears |
| 8,075,576 | B2 | 12/2011 | Eidenschink et al. |
| 9,526,502 | B2 | 12/2016 | Regadas |
| 10,028,739 | B2 | 7/2018 | Alexander et al. |
| 10,085,763 | B2 | 10/2018 | Binmoeller et al. |
| 10,258,320 | B2 | 4/2019 | Dreyfuss et al. |
| 2002/0035311 | A1* | 3/2002 | Ouchi ................ A61B 1/00089 600/156 |
| 2003/0144673 | A1* | 7/2003 | Onuki .............. A61B 17/12013 606/139 |
| 2003/0167071 | A1 | 9/2003 | Martin et al. |
| 2004/0158127 | A1* | 8/2004 | Okada .................... A61B 18/14 600/104 |
| 2006/0122633 | A1* | 6/2006 | To ........................ A61B 17/068 606/139 |
| 2007/0203506 | A1* | 8/2007 | Sibbitt ............... A61B 17/0057 606/139 |
| 2007/0225734 | A1* | 9/2007 | Bell ................. A61B 17/12013 606/139 |
| 2007/0265493 | A1 | 11/2007 | Zirps et al. |
| 2010/0057101 | A1 | 3/2010 | Karpiel |
| 2010/0204716 | A1 | 8/2010 | Stewart et al. |
| 2011/0106107 | A1* | 5/2011 | Binmoeller ........ A61B 17/1285 606/139 |
| 2011/0106116 | A1* | 5/2011 | Ducharme ......... A61B 17/0057 606/151 |
| 2012/0101526 | A1 | 4/2012 | Bennett |
| 2012/0150196 | A1 | 6/2012 | Hoffman et al. |
| 2014/0039549 | A1 | 2/2014 | Belsky et al. |
| 2014/0142596 | A1* | 5/2014 | Knotts ............. A61B 17/00234 606/140 |
| 2014/0276909 | A1* | 9/2014 | Raybin .............. A61B 1/00137 606/113 |
| 2016/0106421 | A1 | 4/2016 | Eliachar et al. |
| 2016/0361066 | A1 | 12/2016 | Wolfe |
| 2021/0128157 | A1 | 5/2021 | Kikuchi et al. |

OTHER PUBLICATIONS

International Search Report and Written Opinion for the International Patent Application No. PCT/US2020/061443, mailed Apr. 13, 2021, 19 pages.

* cited by examiner

DEVICES, SYSTEMS, AND METHODS FOR SECURING TISSUE

PRIORITY

This application claims the benefit of priority under 35 USC § 119 to U.S. Provisional Patent Application Ser. No. 62/941,003, filed Nov. 27, 2019, which is incorporated by reference herein in its entirety and for all purposes.

FIELD

The present disclosure pertains to medical devices. More particularly, the present disclosure pertains to devices, systems, and methods for securing tissue, such as a tissue defect or wound resulting from an endoscopic procedure, e.g., an endoscopic mucosal resection or submucosal dissection procedure.

BACKGROUND

A tissue opening or defect, for example a wound, such as a tissue defect within a body lumen resulting from endoscopic mucosal resection (EMR) or endoscopic submucosal dissection (ESD), may be large enough that it may be difficult to close on its own, or the time for it to close may be prolonged. A risk of infection may increase the longer the wound remains open. Wounds larger than an immediate working area of an endoscope may also be difficult to close using devices that are sized to extend through a working channel of an endoscope. Adjusting a device for gathering or securing tissue may be difficult to achieve a desired amount of tissue within the device.

It is with the above considerations in mind that the improvements of the present disclosure may be useful.

SUMMARY

The present disclosure, in its various aspects, is directed generally to medical devices, and more specifically to devices, systems, and methods for securing tissue. In an aspect, a device for securing tissue may include a loop portion configured to be disposed about a distal end of a delivery device in a delivery configuration and configured to be secured about the tissue in a deployed configuration. A locking member may be disposed on the loop portion. A tether portion having a proximal end may be extendable proximally within the delivery device and a distal portion extending from the loop portion slidably through the locking member.

In various embodiments describe here or otherwise, a plurality of protrusions may be disposed along the loop portion, the protrusions configured to translate with the tether portion in a direction through the locking member. The locking member may include a tab configured to engage the plurality of protrusions. A release element may be slidably disposable through the locking member between the plurality of protrusions and the tab. The release element may include a tubular wall with a radial aperture extending through the wall. The locking member may include a gear configured to accept the tether portion and engage the plurality of protrusions such that rotation of the gear translates the tether portion through the locking member. The protrusions may be configured to at least partially embed into the tissue in the deployed configuration. The locking member may be disposed at an end of the loop portion.

In an aspect, a system for securing tissue may include a delivery catheter having a distal end. The system may include a securing element. A tubular element may be connected to the distal end of the delivery catheter. A filament may extend from the tubular element at a distal portion of the filament. A clamp with opposable arms may be disposed about a proximal portion the filament, the filament forming a tissue securing loop between the distal portion and proximal portion, the clamp slidably disposable within the tubular element, wherein the clamp transitions from an open configuration with the opposable arms at a first distance away from each other to a closed configuration with the opposable arms at a second distance away from each other that is shorter than the first distance as the clamp slides proximally within the tubular element. An actuation wire may extend proximally from a proximal end of the clamp within the delivery catheter.

In various embodiments described here or otherwise, each of the opposable arms may further include a radial extension at a distal end of the clamp, an outer diameter across the extensions in a plane perpendicular to a longitudinal axis of the clamp being wider than an inner diameter of the tubular element. The tubular element may be releasably connected to the delivery catheter at a connection point along the catheter, wherein, in a delivery configuration with the clamp in the closed configuration within the tubular, the tubular element deflects the connection point releasing the tubular element with clamp from the delivery catheter. Proximal movement of the actuation wire may slide the clamp to the closed configuration within the tubular element, which in turn causes the clamp to disconnect from the actuation wire and causes the tubular element to deflect the connection point and release the tubular element from the delivery catheter. A plurality of protrusions may be disposed along an inside surface of each of the opposable arms, the inside surface contacting the proximal portion of the filament in the closed configuration. The filament may be slidable within the clamp when the clamp is in the open configuration and wherein the filament is fixed within the clamp when the clamp is in the closed configuration.

In an aspect, a system for securing tissue may include a securing element having a delivery configuration and configured to substantially close about a portion of the tissue in a deployed configuration. The securing element may include a loop portion configured to be disposed about the end cap in the delivery configuration. A locking member may be disposed on the loop portion. A tether portion having a proximal end may extend from the loop portion slidably through the locking member.

In various embodiments described here or otherwise, a system may include a catheter. The catheter may include a sheath having an inward tapered distal inner diameter. A severing clip may be slidably disposed within the sheath and having edges extending radially inward at a distal end of the clip, the edges of the clips disposed about the tether portion such that distal translation of the clip with respect to the sheath causes the edges to sever the tether portion. The proximal end of the tether portion may include a release element. The catheter may include a plurality of arms at a distal end of the catheter. A distal end of the arms has an inner diameter that is smaller than an outer diameter of the release element. The catheter may include an elongate body slidably disposed within the plurality of arms proximal to the bulb. The arms may be configured such that proximal translation of the catheter relative to the elongate body releases the bulb from the arms. Spring elements may be at a distal end of the catheter configured to bias the arms radially toward each other. The securing element may be disposable about an outer surface at the distal end of catheter. The catheter may be an endoscope with an end cap and the securing element is disposed about the outer surface and the endcap.

BRIEF DESCRIPTION OF THE DRAWINGS

Non-limiting examples of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of skill in the art to understand the disclosure. In the figures.

It is noted that the drawings are intended to depict only typical or exemplary embodiments of the disclosure. Accordingly, the drawings should not be considered as limiting the scope of the disclosure. The disclosure will now be described in greater detail with reference to the accompanying drawings.

DETAILED DESCRIPTION

Various embodiments according to the present disclosure are described below. As used herein, "proximal end" refers to the end of a device that lies closest to the medical professional along the device when introducing the device into a patient, and "distal end" refers to the end of a device or object that lies furthest from the medical professional along the device during implantation, positioning, or delivery.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The detailed description should be read with reference to the drawings, which are not necessarily to scale, depict illustrative embodiments and are not intended to limit the scope of the invention.

A number of medical procedures, including intravascular procedures, procedures along the digestive, urinary, respiratory, reproductive and/or biliary tracts, thoracic procedures, etc., utilize medical devices to access tissue intended for removal (e.g., "target tissue") within the body. For example, in some current medical procedures (e.g., EMR and ESD), physicians may utilize a colonoscope, duodenoscope, bronchoscope, gastroscope, or similar endoscope or other medical device to access and remove diseased lesions, creating a wound or defect in the tissue. A "wound" as used herein may include a defect, injury, bleed, ulcer, lumen opening, or like anatomy, which a medical professional would like to secure or close for sealing, healing, hemostasis, ligation, or the like. In some instances, an endoscope may incorporate features which assist the physician in visualizing and performing the tissue securing procedure. For example, some endoscopes may include a light and/or camera designed to illuminate and/or visualize the body lumen as the endoscope is navigated and positioned adjacent to a target tissue site. Additionally, some endoscopes may also include a lumen (e.g., a working channel) through which a resecting device, grasping member, or other accessory devices may be deployed and utilized. Additional visualization and/or external and/or internal imaging methods may be alternatively or additionally employed, e.g., fluoroscopy.

Medical procedures, e.g., EMR and ESD, may result in portions of tissue, e.g., body lumen or organ tissue, such as a mucosal layer, being resected and/or dissected, resulting in a wound or defect in the tissue. In this context, wound securing, closure, and healing may be aided by one or more devices substantially approximating wound tissue (e.g., wound edges) such that tissue layers are brought together or closer together across the wound for purposes, among others, of facilitating tissue adhesion and eventual healing of the wound, achieving hemostasis, or the like. Another consideration are wounds that are larger than an immediate working area of an endoscope, which may be difficult to close using devices that are sized to extend through a working channel of an endoscope, e.g., wounds larger than about 2 cm in diameter. These larger wounds may benefit from different configurations of securing devices and/or multiple securing devices as well. Although, embodiments are described here with a particular emphasis on wound closure, it is contemplated that the securing devices may be implemented in other applications where acquiring, approximating, and/or securing tissue is desired.

Figure 1A:
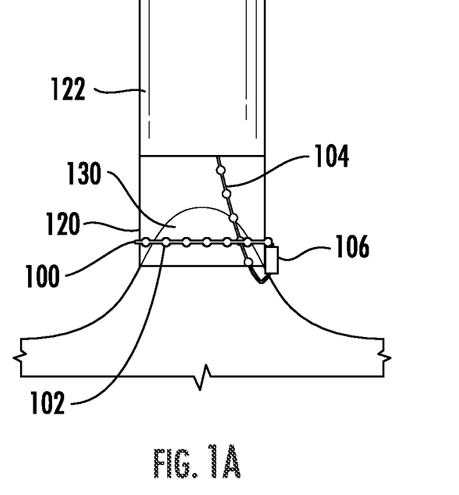
FIG. 1A illustrates a system for securing tissue including an endoscope with a cap having a device about a tissue being displaced within the cap, in accordance with an embodiment of the present disclosure.

Referring to FIG. 1A, a distal end of a delivery device, e.g., an endoscope 122 including an endcap 120, according to an embodiment of the present disclosure, is illustrated as being oriented about a tissue 130 that is displaced at least partially within the endcap 120. The tissue 130 may be displaced within the endcap 120 via a suction and/or vacuum source that is in fluid communication with a channel of the endoscope 122. The suction force may create a negative pressure within the endcap 120 that displaces at least part of the tissue 130 proximally into the endcap 120. In various embodiments, a grasper or other medical tool may be used to position select tissue in addition to or in lieu of suction and/or use of the endcap 120. A securing element 100 for securing the tissue 130 has a loop portion 102 and a tether portion 104. The loop portion 102 is configured to be disposed about a distal end of a delivery device, e.g., the endcap 120, in a delivery configuration. A proximal end of the tether portion 104 extends within the endcap 120 and into the endoscope 122. The tether portion 104 extends from the loop portion 102 slidably through a locking member 106. The locking member 106 is disposed on the loop portion 102 of the securing element 100 such that the loop portion 102 has a first end at the locking member 106 and a second end that extends slidably through the locking member 106 to the tether portion 104. The securing element 100 is shown in the delivery configuration about the endcap 120 with the loop portion 102 of the securing element 100 extended to a diameter wide enough to fit about the endcap 120. In the delivery configuration, the loop portion 102 has an inner diameter that substantially matches the outer diameter of (or a channel within) the endcap 120 and/or the endoscope 122. Because the diameter of the loop portion 102 cannot decrease in the delivery configuration about the endcap 120, the tether portion 104 is prevented from slidably extending through the locking member 106. The endcap 120 positions the closure element 100 distal to and in view of an imaging device, e.g., a camera, of the endoscope 122 for a medical professional to visualize the securing element 100 and surrounding anatomy. The endcap 120 may be substantially translucent and/or transparent such that the medical professional may see through the endcap 120. The securing element 100 may be inserted into a body lumen of a patient in the delivery configuration about the endcap 120. The assembly of the securing element 100 and endcap 120 may be preloaded on the endoscope 122 in packaging or secured to the endoscope prior to insertion into a patient.

Figure 1B:
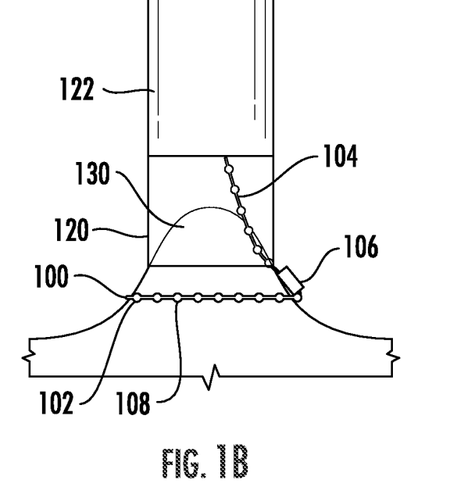
FIG. 1B illustrates the system of FIG. 1A with the device being deployed about the tissue.

Referring to FIG. 1B, with the tissue 130 at least partially displaced proximally within the endcap 120, the tether portion 104 of the securing element 100 may be translated proximally (e.g., pulled) to initiate transition of the securing element 100 from the delivery configuration about the endcap 120, to a deployed configuration about the tissue 130. As the tether portion 104 is translated proximally into the endcap 120 and endoscope 122, the loop portion 102 of the closure element 100 is displaced off of the distal end of the endcap 120 and moves to a position about the tissue 130. The suction force displacing the tissue 130 may be controlled to maintain a desired amount of the tissue 130 in tension within the endcap and allowing the loop portion 102 to be placed about and in contact with the tissue at or slightly beyond the margins of the tissue 130, delineating the portion of tissue which is desired to be removed. As the loop portion 102 is released from the endcap 120 about the tissue 130 via proximal translation of the tether portion 104, the loop portion 102 may transition from the delivery configuration having a larger diameter, to the deployed configuration having a smaller diameter: this is because the loop portion 102 is no longer constrained by the endcap 120 and may be decreased in diameter via further proximal translation of the tether portion 104 sliding the tether portion through the locking member 106, thereby decreasing the diameter of the loop portion 102 about the tissue 130. Sliding the tether portion 104 through the locking member 106 may be assisted by partially or completely fixing the position of the locking member 106 with respect to the tether portion 104 (e.g., by compressing the locking member 106 against the tissue 130 with the endcap 120 or with another tool, or the like). The loop portion 102 includes protrusions 108 that may interact with the locking member 106 (e.g., as will be further discussed in various embodiments herein). The protrusions 108 may be various shapes, e.g., balls, cones, frustums, diamonds, boxes, hooks, tines, barbs, anchors, spikes, disks, rings, a combination thereof, or the like. The protrusions 108 may engage the tissue 130 and may assist in resisting proximal translation of the tether portion 104 and by extension the loop portion 102, such that the loop portion 102 is inhibited or prevented from proximally sliding off of the tissue 130. The tether portion 104 may be further translated proximally through the locking member 106 to adjust the diameter of the loop portion 102 about the tissue 130. A medical professional may adjust the diameter of the loop portion 102 to adjust how the loop portion 102 secures the tissue 130 (e.g., at what position about the tissue, and/or how tightly, etc.).

Figure 1C:
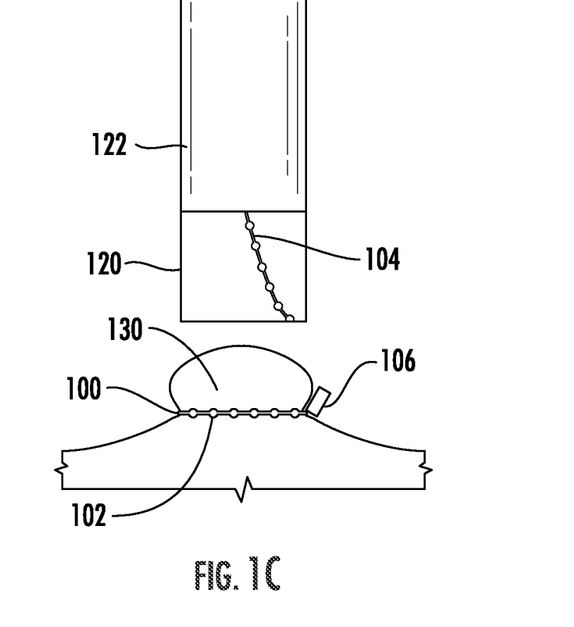
FIG. 1C illustrates the system of FIGS. 1A and 1B with the device in the deployed configuration.

Referring to FIG. 1C, the securing element 100 is in the deployed configuration securing the tissue 130. The securing element 100 is constricted about the tissue 130 with the loop portion 102 having a diameter that is fixed by the locking member 106. The tether portion 104 may be severed at a point along the length of the tether portion 104 proximal to the locking member, by severing or disconnecting devices and methods that will be further described in embodiments herein. The suction force is released and the endcap 120 is proximally translated away from the tissue 130 that is now secured by the securing element 100. Thereafter, the secured tissue 130 may be treated, e.g., by cutting into or cutting off the tissue 130, ablating the tissue 130, or leaving the secured tissue 130 to become necrotic and fall away.

Figure 2A:
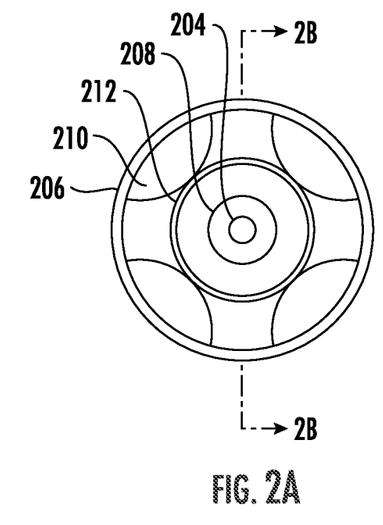
FIG. 2A illustrates an axial view of a locking member of a device for securing tissue, in accordance with an embodiment of the present disclosure.
Figure 2B:
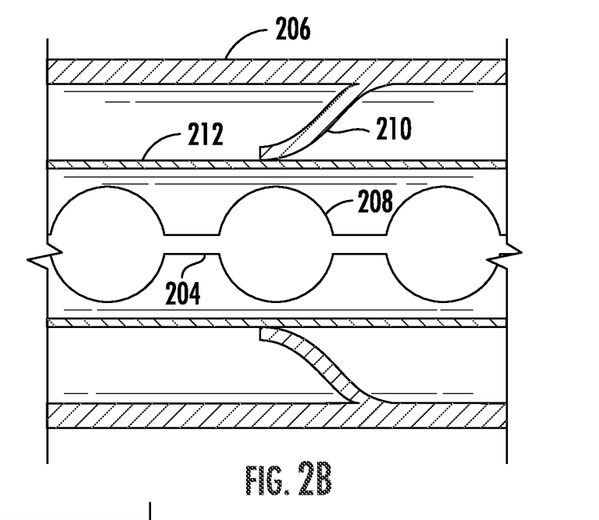
FIG. 2B illustrates a right cross-sectional view of the device of FIG. 2A with a release element slidably disposed through the locking member, in accordance with an embodiment of the present disclosure.

Referring to FIGS. 2A and 2B, a locking member 206 of a device for securing tissue is illustrated according to an embodiment of the present disclosure, which includes a tether portion 204 of the securing device slidably extending through the locking member 206. The locking member 206 includes tabs 210 that are configured to engage protrusions 208 along the tether portion 204. The tabs 210 extend radially within the locking member 206 at an angle such that the tabs 210 are oriented partially in a proximal direction. The tabs 210 each have a length such that they extend within an outer diameter of the protrusions 208 and engage the protrusions 208 as the tether portion 204 is moved through the locking member 206. The tabs 210 may be flexible and/or resilient such that in an unconstrained state the tabs 210 engage with the tether portion 204. A release element 212 may be slidably disposed through the locking member 206, as shown, radially between the protrusions 208 and the tabs 210 in an unlocked configuration. In the unlocked configuration, the tabs 210 are in a constrained state and do not engage with the protrusions 208 such that the tether portion 204 may be slidably extended in a proximal or distal direction through the release element 212 and the locking member 206.

Figure 2C:
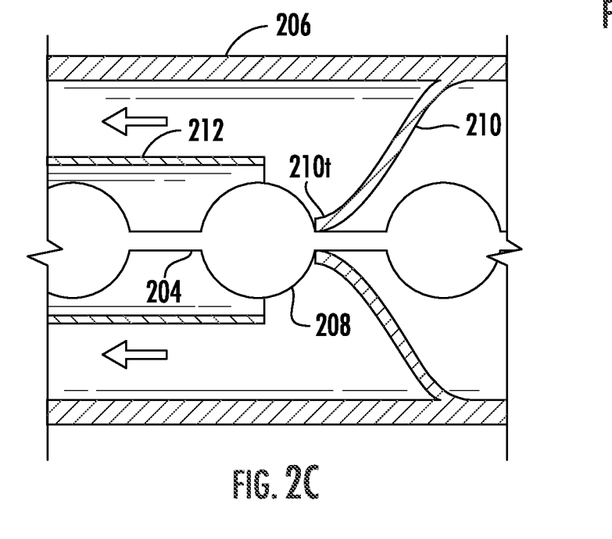
FIG. 2C illustrates a right cross-sectional view of the device of FIGS. 2A and 2B with the release element slidably removed from the locking member.

FIG. 2C illustrates the locking member 206 of FIGS. 2A and 2B in a locked configuration. The release element 212 is proximally translated such that it is no longer in contact with the tabs 210. The tabs 210 are engaged with one of the protrusions 208 such that the tether portion 204 cannot be distally translated through the locking member 206 due to a proximally extending tip 210t of the tabs 210. The tether portion 204 remains free to translate proximally through the locking member 206 because the protrusion(s) 208 is able to engage the tabs 210 in the proximal direction such that the tips 210t may widen to allow the passage of the protrusion(s) 208.

Figure 3A:
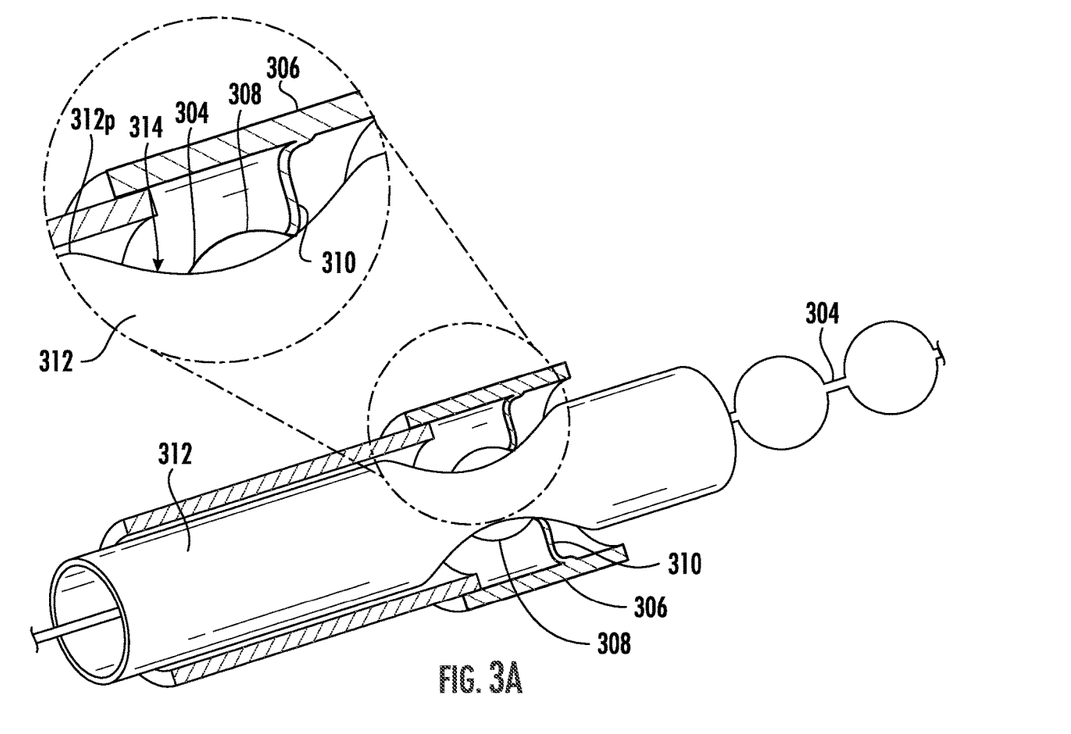
FIG. 3A illustrates a locking member in a locked configuration of a device for securing tissue with a release element having an aperture, in accordance with an embodiment of the present disclosure.

FIG. 3A illustrates a locking member 306 in a locked configuration of a device for securing tissue with a release element 312 having radial apertures 314, in accordance with an embodiment of the present disclosure. The radial apertures 314 allow for the tabs 310 to extend within the release element 312 to engage the protrusions 308 temporarily in the locked configuration. Prior to the locked configuration depicted in FIG. 3A, the tabs 310 may have been engaging a proximal portion 312p of the release element 312 during delivery that is proximal to the apertures 314 in an unlocked configuration. Distal and proximal translation of the release element 312 will manipulate the configuration and relationship between the release element 312 and the tabs 310. The release element 312 extends proximally to out of the patient to a handle that may manipulate proximal and distal translation of the release element 312.

Figure 3B:
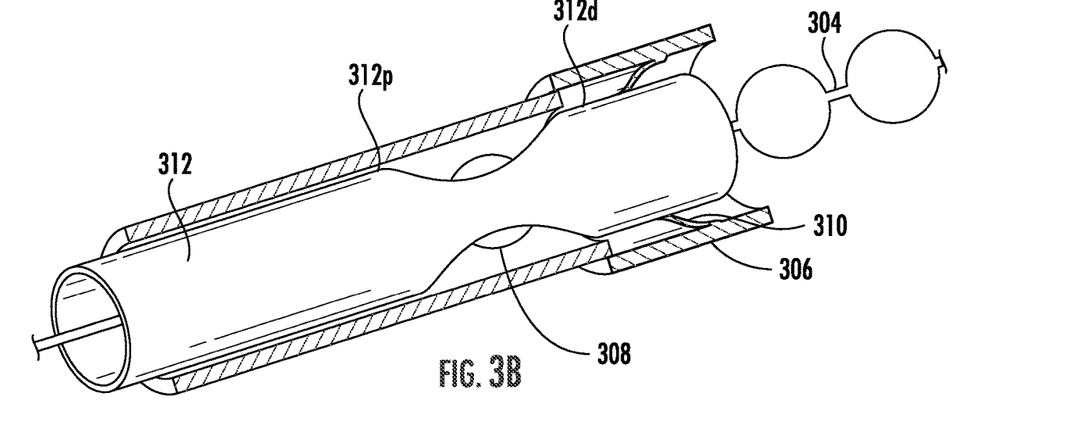
FIG. 3B illustrates the device of FIG. 3A with the locking member in an unlocked configuration.

FIG. 3B illustrates the locking member 306 of FIG. 3A in an unlocked configuration with the tabs 310 engaging a distal portion 312d of the release element 312 that is distal to the apertures 314. The locking member 306 may transition from the temporarily locked configuration of FIG. 3A to the unlocked configuration of FIG. 3B by proximally translating the release element 312 such that the tabs 310 widen as they ride along the outer surface of the release element 312 until the tabs 310 engage the distal portion 312d. In this unlocked configuration, the tether portion 304 may be freely extended proximally or distally through the release element 312 and the locking member 306 to a desired position. If the position of the tether portion 304 in the temporarily locked configuration of FIG. 3A is undesirable (e.g., regarding the position of the loop portion about the tissue), the release element 312 may be manipulated proximally to the unlocked configuration of FIG. 3B for repositioning and/or for other further adjustment of the tether portion 304 or loop portion. Alternatively, if the position of the tether portion 304 in the temporarily locked configuration of FIG. 3A is desirable, the release element 312 may be removed from the locking member 306 such that movement of the tether portion 304 is minimized and a final position of the tether portion 304 within the locking member 306 may be achieved.

Figure 4A:
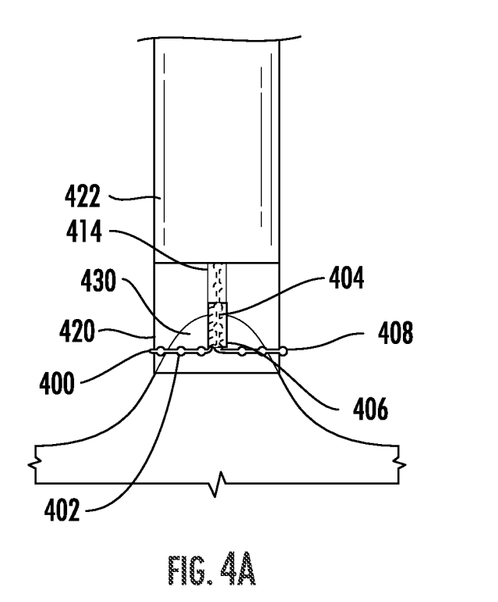
FIG. 4A illustrates a system for securing tissue including an endoscope with a cap having a device about a tissue being displaced within the cap, in accordance with an embodiment of the present disclosure.

Referring to FIG. 4A, a distal end of a delivery device, e.g., an endoscope 422 including an endcap 420, according to an embodiment of the present disclosure, is illustrated as being oriented about a tissue 430 that is displaced at least partially within the endcap 420. A loop portion 402 of a securing element 400 is disposed about the endcap 420 in a delivery configuration. A tether portion 404 of the securing element 400 extends from the loop portion 402 within the endcap 420. A locking member 406 having a gear (e.g., a worm gear, a rack and pinion, or any shape of threads and/or pinions that may correspond to a shape of protrusions 408 of the loop portion 402) is disposed at an end of the loop portion 402. The tether portion 404 extends proximally through the locking member 406 and into a catheter 414. The catheter 414 has a distal end that is connected to the locking member 406 and the catheter 414 may be rotated to operate the gear of the locking member 406.

Figure 4B:
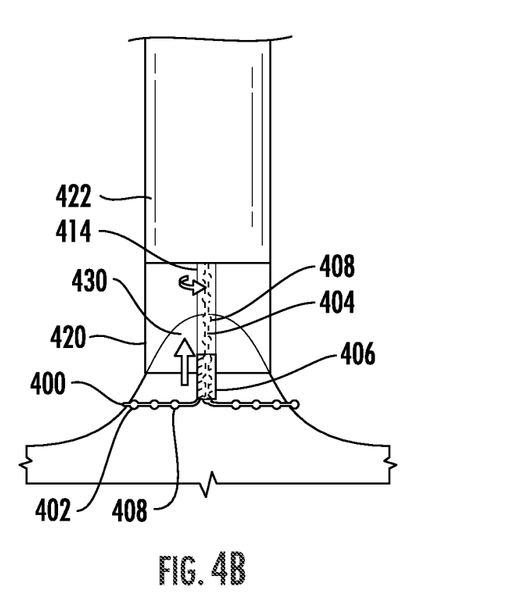
FIG. 4B illustrates the system of FIG. 4A with the device being deployed about the tissue.

Referring to FIG. 4B, the catheter 414 has been proximally translated and/or rotated such that the tether portion 404 has been proximally translated within the endcap 420. Proximally translating the catheter 414 also proximally translates the tether portion 404 because both the catheter 414 and the tether portion 404 are connected to the locking member 406. Rotating the catheter 414 may proximally (or distally) translate the tether portion 404 because rotating the catheter 414 operates the gear of the locking member 406 to engage and translate protrusions 408 disposed along the tether portion 404. The gear may be in a fixed position while not being rotated or engaged by the catheter 414. FIG. 4B illustrates the loop portion 402 being initiated from the delivery configuration about the endcap 420, to a deployed configuration about the tissue 430. As the tether portion 404 is translated proximally into the endcap 420, catheter 414, and endoscope 422, the loop portion 402 of the closure element 400 is displaced off of the distal end of the endcap 420 and moves to a position about the tissue 430. The size of the diameter of the loop portion 402 may be adjusted by rotating the catheter 414 that operates the locking member 406 translating the tether portion 404. The gear may be rotated about its axis such that one or more threads of the gear engage one or more protrusions 408 to translate the protrusion proximally or distally thereby tightening or loosening the loop portion 402.

Figure 4C:
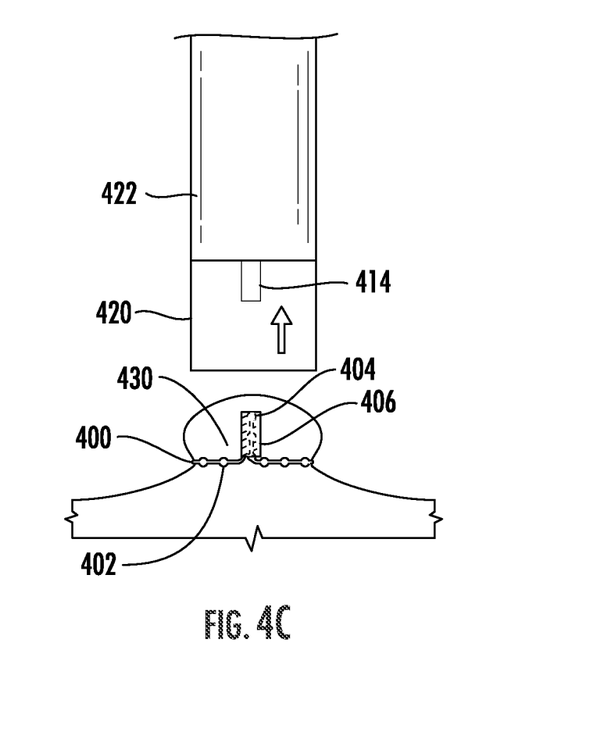
FIG. 4C illustrates the system of FIGS. 4A and 4B with the device in the deployed configuration.

Referring to FIG. 4C, the tether portion 404 is severed along its length and the catheter 414 is disconnected from the locking member 405 with the securing element 400 fixed within the locking member 405. The suction is disengaged and the endcap 420 and catheter 414 are proximally withdrawn from the tissue 430, leaving the securing element 400 including the loop portion 402, locking member 406, and tether portion 404 in the deployed configuration securing the tissue 430. In various embodiments, a securing element 400 may not include protrusions 408. A tether portion 404 of securing element 400 without protrusions 408 may be translated through a locking member 405. The tether portion 404 may be twisted, knotted, and/or tied via manipulation of the tether portion 404 by the catheter 414 or a medical instrument such that the tether portion is locked and cannot translate back through the locking member 405 toward the loop portion 402. The tether portion 404 may be sufficiently twisted, knotted, and/or pulled such that the tether portion 404 is severed from the locking member 405.

Figure 5A:
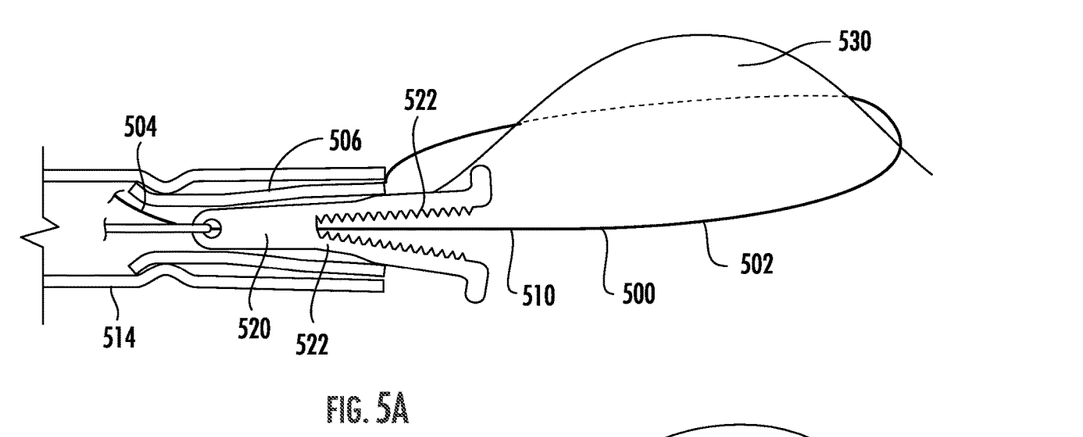
FIG. 5A illustrates a system for securing tissue including a catheter with a securing element in a delivery configuration, in accordance with an embodiment of the present disclosure.

Referring to FIG. 5A, a system for securing tissue according to an embodiment of the present disclosure is illustrated, which includes a securing element 500 connected to a delivery catheter 514. The securing element 500 includes a locking member 506 with a tubular element that is connected to a distal end of the delivery catheter 514. The delivery catheter 514 is crimped to the locking member 506 at a connection point 516 along the catheter 514 in a delivery configuration. A filament 510 extends from the locking member forming a loop portion 502 and a tether portion 504. The filament 510 is slidably disposed through a clamp 520. The clamp 520 has opposable arms 522 and may slide into the locking member 506. In FIG. 5A, the opposable arms 522 are open and apart from each other in the delivery configuration with the clamp 520 only partially within the locking member 506. The securing element 500 may be inserted into a body lumen of a patient in the delivery configuration. The position of the clamp 520 with respect to the locking member 506 may be controlled via proximal and distal translation of an actuation wire 528 extending from a proximal end of the clamp 520 within the delivery catheter 514. The loop portion 502 of the filament 510 may be oriented about a tissue 530 for securing the tissue 530.

Figure 5B:
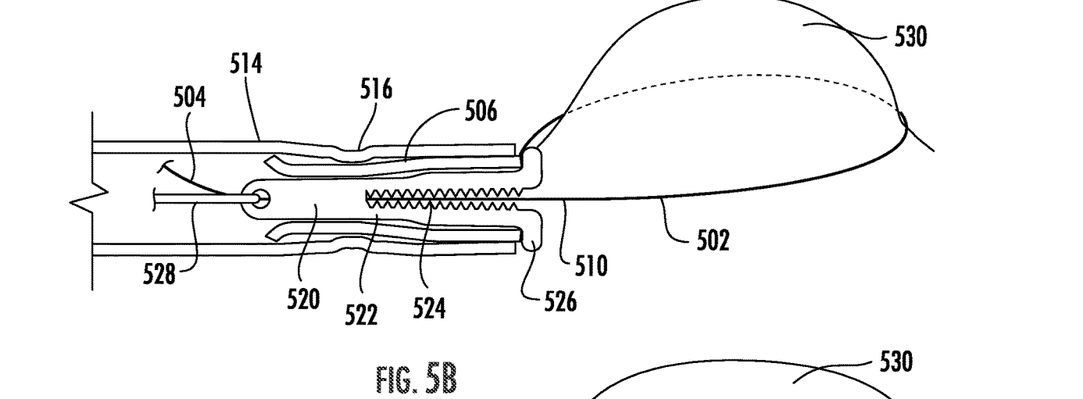
FIG. 5B illustrates the system of FIG. 5A with the securing element being deployed about a tissue.

Referring to FIG. 5B, the clamp 520 is transitioned towards the deployed configuration within the locking member 506 via a proximal translation of the actuation wire 528. As the clamp 520 is translated into the locking member 506, the locking member 506 forces the arms 522 to close towards each other about the filament 510. Inwardly oriented radial protrusions 524 may be included on inside surfaces of the arms 522, as shown, to engage the filament 510, thereby fixing a diameter of the loop portion 502 about the tissue 530. Once fixed, the filament 510 is no longer translatable within the clamp 520 by proximally translating the tether portion 504 because the filament 510 is compressed by the arms 522 and protrusions 524. Further proximal translation of the actuation wire 528 translates radial extensions 526 at a distal end of the clamp 520 having an outer diameter across the extensions 526 in a plane perpendicular to a longitudinal axis of the clamp being wider than an inner diameter of the locking member 506 against the locking member 506 and function as a backstop as to how far the clamp 520 may be pulled into the locking member 506. The clamp 520 is proximally translated such that the locking member 506 disrupts (e.g., moves, deforms, flattens) the connection point 516, releasing the locking member 506 from the delivery catheter 516. Further proximal translation of the actuation wire 528 and the tether portion 504 severs the actuation wire 528 and tether portion 504 from the clamp 520. Severing of the actuation wire 528 and/or the tether portion 504 may be performed by sufficient shear force between the clamp 520 and the wire 528 or tether portion 504 (e.g., from proximal translation of the wire 528 and/or tether portion 504). The wire 528 and/or the tether portion 504 may be cut by a medical instrument or a sharp edge disposed within the delivery catheter 514. In various embodiments, a the wire 528 and/or tether portion 504 may be coupled to a hook-like elongate body, whereby proximal translation of the hook-like elongate body may deform or destroy the hooked shape of the hook-like elongate body, releasing the wire 528 and/or the tether portion 504.

Figure 5C:
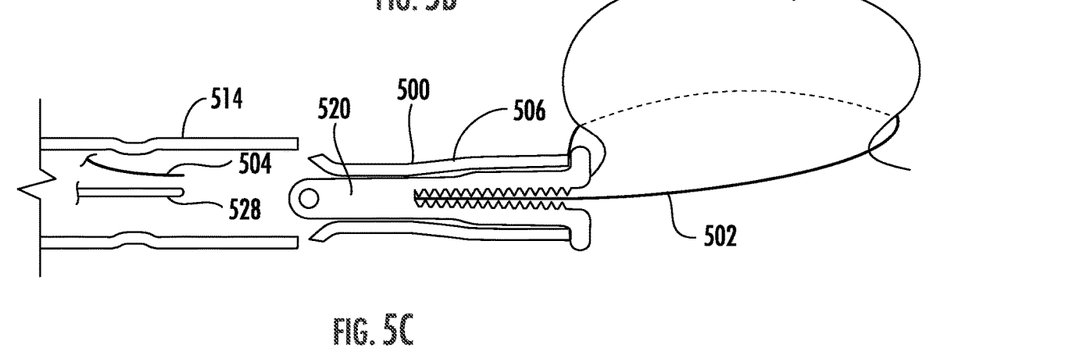
FIG. 5C illustrates the system of FIGS. 5A and 5B with the securing element in the deployed configuration.

Referring to FIG. 5C, the securing element 500 is in the deployed configuration securing the tissue 530. The securing element 500 is constricted about the tissue 530 with the loop portion 502 having a diameter that is fixed by the locking member 506. The tether portion 504 is severed along the length of the tether portion 504 by a severing or disconnecting method that will be further described in embodiments herein. The catheter 514 and actuation wire 528 are proximally translated away from the tissue 530 for removal from the patient.

Figure 6:
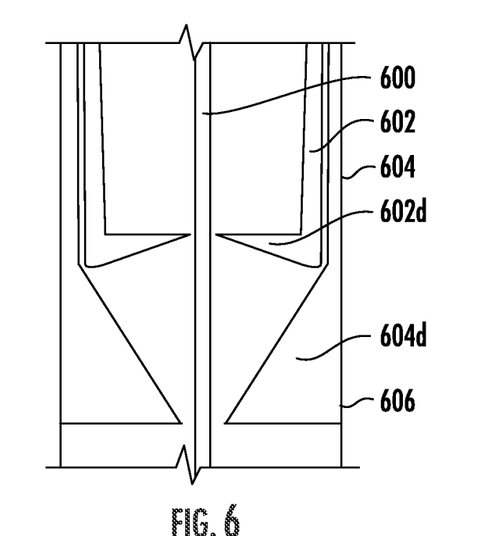
FIG. 6 illustrates a catheter having a clip slidably disposed within a sheath about a portion of device for securing tissue, in accordance with an embodiment of the present disclosure.

With reference to FIG. 6, a tether portion 600 of a device may be severed by a system including a catheter including a sheath 604, according to an embodiment of the present disclosure. The sheath 604 is slidably disposed about the tether portion 600. The sheath 604 has a distal portion 604d having a proximally tapering inner surface that has an inner diameter smaller than a remainder inner diameter of the sheath 604. A clip 602 having edges 602d extending radially within the clip 602 at a distal end of the clip 602 is slidably disposed within the sheath 604 and about the tether portion 600. Distal translation of the clip 602 with respect to the sheath 604 (i.e., proximal translation of the sheath 604 with respect to the clip 602) radially collapses the edges 602d about the tether portion 600 thereby severing the tether portion 600.

Figure 7A:
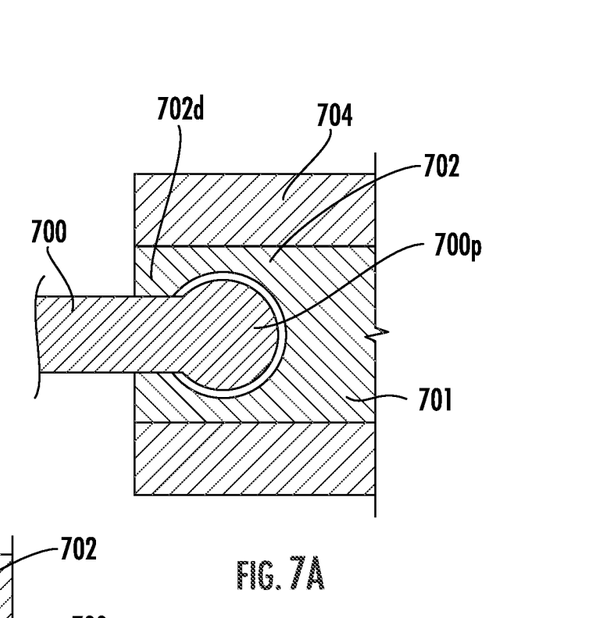
FIG. 7A illustrates a portion of a device for securing tissue attached to a distal end of a catheter, in accordance with an embodiment of the present disclosure.

With reference to FIG. 7A, a system according to an embodiment of the present disclosure includes a tether portion 700 of a device that may be disconnected from a delivery catheter or endoscope. A bulb 700p is included at a proximal end of the tether portion 700. The system includes a catheter 701 having two (or possibly more) arms 702 at a distal end of the catheter 701. The bulbous mass 700p is substantially contained with the arms 702. The arms 702 each have a distal end 702d that together form an inner diameter that is smaller than an outer diameter of the bulbous mass 700p. A sheath 704 may protect the tether portion 700 and catheter 701 from interference with other devices or anatomies. The sheath 704 may include the working channel of an endoscope which may be used to deliver the catheter. Alternatively, the sheath 704 may not be employed with the catheter 701, and the arms 702 may protect the bulbous mass 700p and the distal ends 702d.

Figure 7B:
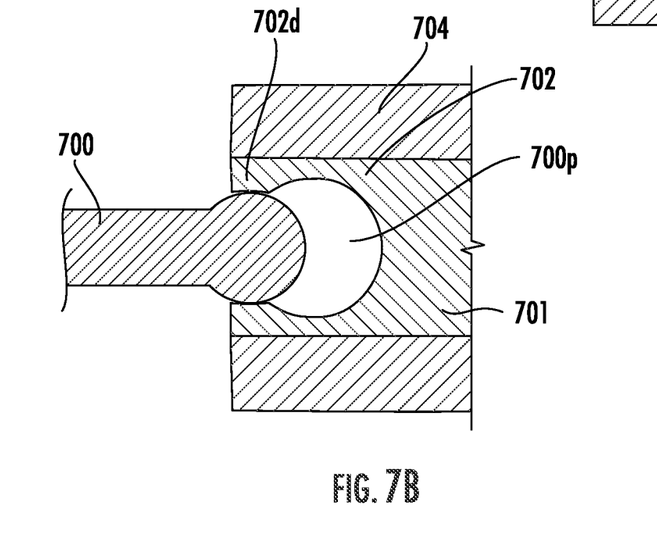
FIG. 7B illustrates the portion of FIG. 7A being disconnected from the catheter.

Referring to FIG. 7B, proximal translation of the catheter 701 with respect to the bulbous mass 700p with a sufficient force may plastically or elastically deform the distal end(s) 702d of the arm(s) and/or the bulbous mass 700p such that the bulbous mass 700p is released from the arms 702 and the tether portion 700 is disconnected from the catheter 701 within the sheath 704. In various embodiments, an elongate body may be slidably disposed within the arms 702 proximal to the bulbous mass 700p. The elongate body may assist with fixating or distally translating the bulbous mass 700p with respect to the arms 702 of the catheter 701 as the catheter 701 is proximally translated with respect to the bulbous mass 700p to disconnect the tether portion 700. In various embodiments, the sheath 704 may include a spring portion at a distal end of the sheath that is configured to bias the arms 702 radially toward each other.

In various embodiments, a medical professional may attach an endcap to an endoscope, a catheter, or the like. The medical professional may load one or more securing elements onto the endcap. The one or more securing elements may include a tether portion extending within the endcap and may be attached to a handle. The endoscope and assembly may be inserted into a patient. A target tissue may be located. The endcap may be oriented toward the tissue. The tissue may be displaced into the endcap. A loop portion of the one or more securing elements may be deployed about the wound by the medical professional manipulating the tether portion and fixing the loop about the tissue.

In various embodiments, a securing element may comprise a material such as nitinol, stainless steel, nickel titanium, an alloy, a polymer, a rubber, nylon, combinations thereof, or the like. Securing elements may have a shape and/or shape-memory set by a mandrel. A securing element may be heat set at a diameter (e.g., a diameter of about 1 mm to about 5 mm, or the like) that may be selectable based on wound geometry and size.

In various embodiments, an endcap as described and illustrated herein may be coupled to an endoscope, catheter, and/or working channel (e.g., insertable, adhered, manufactured as a unibody, etc.). An endcap may additionally or in the alternative be an extension of an endoscope, catheter, and/or working channel.

Devices according to the embodiments described, and in accordance with other embodiments of the present disclosure, alone or in a system or kit or as part of a method or procedure, including with other accessories, may be used in cavities, lumens, tracts, vessels and organs of the body, such as to access, treat or diagnose conditions in the peritoneal, abdominal, bronchial or thoracic cavities, vascular vessels, gastrointestinal or urinary tract, uterus, bladder, lung and liver organs, etc.

Variations, modifications, and other implementations of the present disclosure in addition to the various embodiments described herein will occur to those of ordinary skill in the art. Accordingly, the present disclosure is to be defined not by the preceding illustrative description but instead by the following claims:

What is claimed is:

1. A device for securing tissue, the device comprising:
a loop portion configured to be disposed on a distal end of a tubular wall of a delivery device, external to and encircling a outer surface of the distal end of the tubular wall of the delivery device in a delivery configuration, and configured to be secured about the tissue in a deployed configuration;
a locking member disposed on the loop portion external to the tubular wall of the delivery device when the loop portion is in the delivery configuration; and
a tether portion extending from the loop portion slidably through the locking member and proximally through a lumen defined longitudinally through the tubular wall of the delivery device to a proximal end of the tubular wall of the delivery device, and proximally actuatable to move proximally through the lumen of the tubular wall of the delivery device to cause distal deployment of the loop portion off the outer surface of the distal end of the tubular wall of the delivery device and onto and encircling the tissue.

2. The device of claim 1, wherein the locking member is shiftable between a locked configuration in which the locking member permits translation of the tether portion in a proximal direction and prevents translation of the tether portion in a distal direction, and an unlocked configuration in which the tether portion is free to translate both in the proximal direction as well as the distal direction.

3. The device of claim 2, wherein the locking member comprises a gear configured to accept the tether portion and engage the plurality of protrusions such that rotation of the gear translates the tether portion through the locking member.

4. The device of claim 1, wherein the loop portion includes a plurality of protrusions and the locking member comprises a tab extending radially inwardly within the locking member when in a locked configuration to engage one of the plurality of protrusions to inhibit distal translation of the tether portion.

5. The device of claim 4, further comprising a release element slidably disposable through the locking member between the plurality of protrusions and the tab to move the tab into a constrained state disengaged from the one of the plurality of protrusions to shift the locking member into an unlocked configuration allowing the tether portion to translate in a proximal direction as well as a distal direction.

6. The device of claim 5, wherein the release element comprises a tubular wall, with the plurality of protrusions slidably extendable therethrough.

7. The device of claim 4, wherein the plurality of protrusions are configured to at least partially embed into the tissue in the deployed configuration.

8. The device of claim 1, wherein the locking member is disposed at an end of the loop portion.

9. The device of claim 1, wherein the loop portion has an inner diameter matching the outer diameter of the distal end of the delivery device and which cannot be decreased when in a delivery configuration encircling the outer surface of the distal end of the tubular wall of the delivery device, and the tether portion is thereby prevented from slidably extending proximally through the locking member when the loop portion is in the delivery configuration.

10. A system for securing tissue, the system comprising:
a delivery device having a distal end and comprising a tubular wall having a distal end and a proximal end and defining an outer surface and a lumen extending longitudinally therethrough between the distal end of the tubular wall and the proximal end of the tubular wall; and
a securing element, the securing element comprising:
a loop portion configured to be disposed on a distal end of the tubular wall of the delivery device, external to and encircling the outer surface of the distal end of the tubular wall of the delivery device in a delivery configuration and configured to be secured about the tissue in a deployed configuration;
a locking member disposed on the loop portion external to the tubular wall of the delivery device when the loop portion is in the delivery configuration; and
a tether portion extending from the loop portion through the locking member and proximally through the lumen defined through the tubular wall of the delivery device to be pulled proximally through the lumen to transition the securing element from the delivery configuration to the deployed configuration encircling the tissue.

11. The system of claim 10, wherein the delivery device is an endoscope.

12. The system of claim 10, further comprising a plurality of protrusions disposed along the loop portion, the plurality of protrusions configured to translate with the tether portion in a direction through the locking member.

13. The device of claim 12, wherein the locking member comprises a tab configured to engage the plurality of protrusions.

14. A system for securing tissue, the system comprising:
an end cap comprising a tubular wall defining a lumen longitudinally therethrough, and having a proximal end engageable with a distal end of an endoscope;
a securing element having a delivery configuration, and configured to substantially close about a portion of the tissue in a deployed configuration, the securing element comprising:
a loop portion configured to be disposed on the end cap, external to and encircling an outer surface of the tubular wall of the end cap in the delivery configuration;

a locking member disposed on the loop portion external to the end cap when the loop portion is in the delivery configuration; and a tether portion extending from the loop portion slidably through the locking member and proximally through the lumen defined longitudinally through the tubular wall of the end cap to a proximal end, and proximally actuatable through the lumen defined through the tubular wall of the end cap to cause distal deployment of the loop portion off the outer surface of the tubular wall of the end cap;

wherein the end cap positions the securing element distal to and in view of an imaging device of the endoscope and is transparent and/or translucent to permit viewing of the securing element by the endoscope when the loop portion is encircling the outer surface of the tubular wall of the end cap.

15. The system of claim 14, further comprising a catheter, the catheter comprising:

a sheath having an inward tapered distal inner diameter; and a severing clip slidably disposed within the sheath and having edges extending radially inward at a distal end of the clip, the edges of the clip disposed about the tether portion such that distal translation of the clip with respect to the sheath causes the edges to sever the tether portion.

16. The system of claim 14, further comprising a catheter, wherein:

the proximal end of the tether portion comprises a release element;

the catheter comprises a plurality of arms at a distal end of the catheter; and a distal end of the plurality of arms arms has an inner diameter that is smaller than an outer diameter of the release element.

17. The system of claim 16, wherein the catheter further comprises an elongate body slidably disposed within the plurality of arms proximal to a bulb.

18. The system of claim 16, wherein the plurality of arms are configured such that proximal translation of the catheter relative to the elongate body releases a bulb from the plurality of arms.

19. The system of claim 16, further comprising spring elements at a distal end of the catheter configured to bias the plurality of arms radially toward each other.

20. The system of claim 14, wherein the tether portion is extendable from the locking member proximally within the tubular wall of the end cap and the endoscope with which the end cap is engaged and is actuatable to cause deployment of the locking member with the loop portion off the distal end of the end cap and onto and encircling the tissue.

* * * * *